United States Patent [19]

Aizawa et al.

[11] Patent Number: 5,362,918
[45] Date of Patent: Nov. 8, 1994

[54] PROCESS FOR PRODUCING ACETALDEHYDE DIMETHYLACETAL

[75] Inventors: Toshiyuki Aizawa; Hitoshi Nakamura; Kunitoshi Wakabayashi; Tetsuo Kudo; Hiroyuki Hasegawa, all of Oita, Japan

[73] Assignee: Showa Denko K.K., Tokyo, Japan

[21] Appl. No.: 51,280

[22] Filed: Apr. 23, 1993

[30] Foreign Application Priority Data

Apr. 24, 1992 [JP] Japan ................................. 4-106696
Apr. 24, 1992 [JP] Japan ................................. 4-106697
Apr. 24, 1992 [JP] Japan ................................. 4-106698

[51] Int. Cl.$^5$ .......................... C07C 41/56; B01D 3/34
[52] U.S. Cl. .................................. 568/594; 568/605; 568/699; 203/68; 203/70
[58] Field of Search ................. 568/564, 605, 699; 203/68, 70

[56] References Cited

U.S. PATENT DOCUMENTS 1,850,836  3/1932  Guinot ................................. 568/594
3,127,450  3/1964  Lorette et al. .
4,613,411  9/1986  Hsu et al. .

FOREIGN PATENT DOCUMENTS 716541  10/1954  United Kingdom ................. 568/594
1379444  1/1975  United Kingdom .

OTHER PUBLICATIONS

Patent Abstracts of Japan, vol. 14, No. 197 (C-712)(4140) 23 Apr. 1990.

Primary Examiner—Howard T. Mars
Attorney, Agent, or Firm—Sughrue, Mion, Zinn, Macpeak & Seas

[57] ABSTRACT

A process for producing acetaldehyde dimethylacetal comprising reacting acetaldehyde and methanol in the presence of an acid catalyst is disclosed, in which the reaction is carried out in a part of a rectification tower while conducting rectification to withdraw the water by-produced from the bottom of the tower and to recover a distillate containing the acetaldehyde dimethylacetal produced from the top of the tower. The distillate is subjected to azeotropic distillation in the presence of n-hexane or cyclohexane to separate methanol as an azeotrope with n-hexane or cyclohexane and a small amount of the acetaldehyde dimethylacetal and to recover high purity acetaldehyde dimethylacetal as a bottom.

7 Claims, 1 Drawing Sheet

PROCESS FOR PRODUCING ACETALDEHYDE DIMETHYLACETAL

FIELD OF THE INVENTION

This invention relates to a process for producing acetaldehyde dimethylacetal, and more particularly an industrially advantageous process for preparing and isolating acetaldehyde dimethylacetal.

BACKGROUND OF THE INVENTION

Di-lower alkylacetals, such as acetaldehyde dimethylacetal, acetaldehyde diethylacetal, acetaldehyde dipropylacetal, and acetaldehyde dibutylacetal, are industrially useful compounds as, for example, intermediates for synthesizing various industrial materials, especially alkyl vinyl ethers which are useful as organic solvents, synthetic perfumes, synthetic resins, and adhesives, and N-vinylcarboxylic acid amides which are starting materials for hydrophilic polymers.

Di-lower alkylacetals are usually prepared by reacting acetaldehyde with a lower alcohol in the presence of an acid catalyst. It is generally accepted that the difference of the starting lower alcohol in kind makes no noticeable different in the mode of the unit reaction. However, as a matter of course, the kinds of the reaction product and by-product vary according to the starting alcohol. The physical properties of the acetal product which greatly influence separation and purification steps, such as distillation characteristics, crystallizability, compatibility with solvents, and distribution coefficient, largely depend on the starting material. Particularly in the production on an industrial scale, factors other than the reactivity of starting materials, for example, the cost, availability, easy handling of starting materials, the final yield of a desired product after isolation and purification, simpleness of the total production line inclusive of isolation and purification steps, the cost of the plant, ease in operation and maintenance, and the cost of utility, are also of great importance. Accordingly, the process to be adopted, inclusive of material selection, should be decided taking all these factors into due consideration.

Various proposals for the mode of process per se for preparing a di-lower alkylacetal from an aldehyde and a lower alcohol have been made to date. For example, a process of using allyl alcohol is disclosed in JP-A-3-246247 (the term "JP-A" as used herein means an "unexamined published Japanese patent application"). The reaction as disclosed being an equilibrium reaction, the result obtained is no more than the conversion at equilibrium. JP-A-62-116534 describes a process starting with an alcohol having 4 carbon atoms. This process requires a large quantity of calcium chloride as a catalyst and a dehydrating agent for achieving satisfactory reaction results. Besides, the process involves extra steps after the reaction, e.g., removal of the catalyst and washing of the reaction mixture.

Various studies have also been given to production of acetaldehyde dimethylacetal from acetaldehyde and methanol, and use of an acid catalyst, such as hydrochloric acid, sulfuric acid, an organic sulfonic acid, an inorganic solid acid (e.g., zeolite) or an ion-exchange resin is generally known, as described in U.S. Pat. Nos. 3,641,163 and 2,840,615, JP-B-62-59097 and JP-B-62-41492 (the term "JP-B" as used herein means an "examined published Japanese patent application"). Similarly to the cases of using other lower alcohols, this reaction as such has a limited conversion by nature of the equilibrium reaction. In order to increase the yield, therefore, it would be necessary to take some manipulation, for example using one of the reactants in large excess or quickly driving out the reaction product from the reaction system. Since the system after reaching to equilibrium in the reaction usually contains by-produced water and the unreacted acetaldehyde in addition to the desired acetal, distillation of the reaction mixture in which the catalyst has been neutralized or from which the catalyst has been removed tends to induce decomposition of the desired dimethylacetal or by-production of undesired impurities.

In the production of dimethylacetal, too, calcium chloride may be used as a catalyst and a dehydrating agent for removing the by-produced water to improve the conversion. However, it must be added in large quantities. This causes an extra cost for water discharge and handling complexity. Removal of by-produced water by azeotropic distillation by using an inert solvent, such as n-heptane or toluene, is also known, but the process involves an extra step for separating and recovering the solvent and cannot be regarded beneficial. While appropriate combinations of these techniques have also been proposed, the outstanding problems still remain unsolved.

In general, a reaction system called a reactive distillation process in which the reaction is carried out while conducting distillation to improve the equilibrium conversion and an apparatus therefor are known as a means for overcoming the drawbacks associated with an equilibrium reaction, such as limitation of a conversion, and there have been reported many cases for equilibrium reactions using an acid catalyst, for example, an esterification reaction (see JP-A-63-277645), an etherification reaction (see JP-A-1-316337), and an acetal reaction (see JP-B-62-29419 and JP-A-3-56134).

The reactive distillation process is considerably influenced by distillation characteristics of various substances present in the reaction system, i.e., starting compounds, the product, by-products, etc., as well as the above-mentioned problems. It is therefore especially important to decide the whole production line taking into account the kinds of the starting materials and the catalyst the reaction conditions, the reaction operation, and the isolation step.

For example, JP-B-62-29419 proposes to prepare an acetal of an unsaturated alcohol having 3 or more carbon atoms by reactive distillation using nitric acid having a relatively low boiling point as a catalyst. However, the process proposed, when applied to synthesis of acetaldehyde dimethylacetal from methanol and acetaldehyde which are the cheapest alcohol and aldehyde, it turned out substantially impractical because the desired acetal product and nitric acid both run from the top of the tower to produce an undesired high-boiling by-product.

JP-A-3-56134 proposes a reactive distillation apparatus for carrying out an equilibrium reaction using a solid acid or a solid base as a catalyst, which is characterized by forcedly circulating the reaction mixture in the reactor. This apparatus is effective where a formalin aqueous solution containing a large quantity of water, which is the main cause of catalyst deterioration, is used as a starting material, that is, in the production of methylal from methanol and a formalin aqueous solution, because of ease in frequent regeneration and exchange of the catalyst. Nevertheless, the apparatus requires additional equipment, such as a pump, which unavoidably entails the cost of construction and operation.

Where a reactive distillation system is applied to the production of acetaldehyde dimethylacetal, since the acetaldehyde dimethylacetal produced and methanol form an azeotropic mixture, a special manipulation should be taken for separation of the acetal and methanol. To this effect, JP-A-58-103331 proposes to conduct azeotropic distillation of a methanol-methylal mixed system by a combination of distillation under pressure and distillation under normal pressure or reduced pressure, utilizing the fact that the proportion of the azeotropic composition varies by changing the pressure of distillation. However, even with the pressure condition varied, the closeness of the boiling points of these two components necessitates great increases in the number of plates of the distillation tower and reflux ratio, which entails the high cost for operation and construction.

German Patent 1007311 proposes extractive distillation with water for a methanol-dimethylacetal system. Apart from difficulty in completely removing methanol, the process has the problem that the acetal obtained contains water, and the water must be removed by azeotropic distillation or with a desiccator, which is not only troublesome but accompanied with a loss in yield.

JP-B-38-19707 suggests to separate an acetal-alcohol system by extractive distillation using an alcohol or an amino compound. However, when such a reactive compound is added to the system and heated, the system suffers an unfavorable side reaction, such as decomposition of the desired product or production of impurities, only resulting in reductions in purity and yield of the product.

It is generally known that a mixture having a nearly azeotropic composition may be separated by distillation in the presence of an azeotrope former (solvent) as a third component. The azeotrope former to be added is chosen according to requirements: (1) to form an azeotrope whose azeotropic point is lower than that of a methanol-acetal azeotrope with a great difference sufficient for effective separation of the acetal, (2) to form an azeotrope having a high methanol content from the energy consideration, and (3) to be inert to the acetal. For the time being, no azeotropic former satisfying all these requirements has been suggested.

SUMMARY OF THE INVENTION

An object of the present invention is to provide a process for producing acetaldehyde dimethylacetal through simple and easy operation in a satisfactory final yield. That is, the object of the present invention is to provide a process which is simpler to carry out than the conventional processes in terms of selection of starting materials, operation, and isolation and purification of the product without requiring expensive equipment while achieving good efficiency.

Under the above-mentioned circumstances, the present inventors have extensively investigated the whole production line with considerations given to the starting materials, catalysts, reaction conditions, reaction operation, and separation steps and, as a result, have found the optimal combination of these factors.

The present invention relates to a process for producing acetaldehyde dimethylacetal (hereinafter simply referred to as "the acetal") comprising reacting acetaldehyde and methanol in the presence of an acid catalyst in a part of a rectification tower while conducting rectification to withdraw the water by-produced from the bottom of the tower and to recover a distillate containing the acetal produced from the top of the tower.

DETAILED DESCRIPTION OF THE INVENTION

Figure 1:
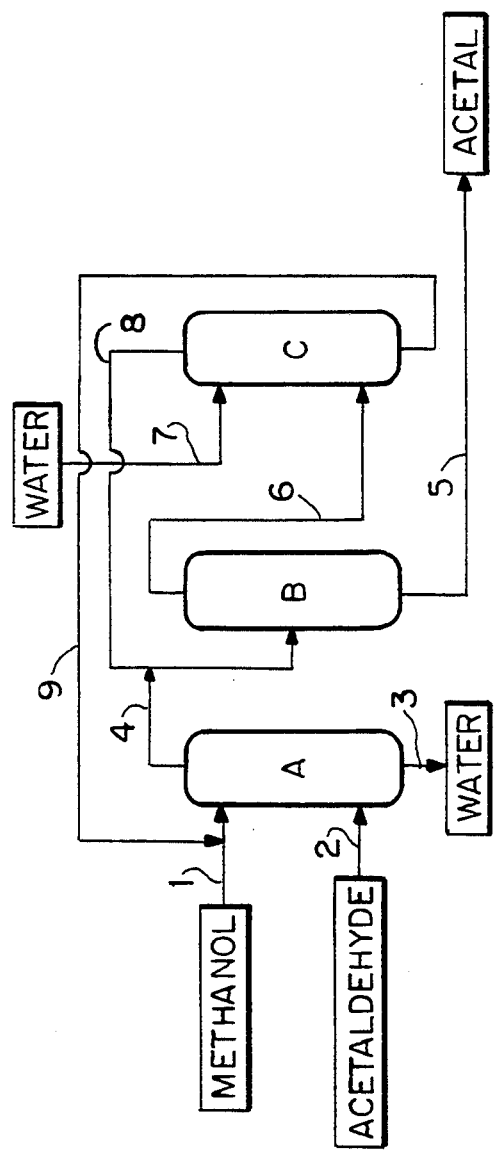
FIG. 1 is a flow diagram illustrating a typical line of production of a high purity acetal according to the present invention.

The acid catalyst which can be used in the process of the present invention is not particularly limited. Examples of usable acid catalysts are homogeneous catalysts such as mineral acids, e.g., hydrochloric acid, sulfuric acid, phosphoric acid, and nitric acid; heteropolyphosphoric acids, e.g., phosphotungstic acid; and organic acids, e.g., p-toluenesulfonic acids, and heterogeneous catalysts such as sulfonic acid type strongly acidic ion exchange resins (commercially available under trade names "Amberlist", "Amberlite" and "Dowex"); sulfonic acid type fluorinated alkylene resins, e.g., a sulfonated tetrafluoroethylene resin; and inorganic solid acids, e.g., mordenite and zeolite. In the present invention, nonvolatile or high-boiling liquid strong acids, e.g., sulfuric acid, phosphoric acid and p-toluenesulfonic acid; and heterogeneous acid catalysts, e.g., resins and solid acids are preferred because of easy separation from the reaction product and no need for the distillate to be neutralized.

The amount of the acid catalyst to be used is not critical. In the case of homogeneous catalysts, while not limiting, they are suitably used in an amount of from about 0.01 to 2% by weight, and preferably from about 0.05 to 1% by weight, based on the total weight of acetaldehyde and methanol. In the case of heterogeneous catalysts, they are used in such an amount that the total amount of acetaldehyde and methanol to be fed is 0.1 to 10,000 times, preferably 1 to 1,000 times the amount of the catalyst, per hour.

The reactive distillation apparatus which can be used for carrying out the process of the present invention is not particularly limited in structure as long as it has a tower system composed of a reactor and a rectification tower connected in series. A rectification tower with the number of theoretical plates of 1 to 100, preferably 5 to 50, is usually used as the rectification portion. The structure of the rectification tower is arbitrary. For example, usable plate towers include those using a bubble cap tray, a uniflux tray, a flexi tray, a Natta float tray, a ballast trays, a perforated tray, a cascade tray, a venturi tray, a Kittel tray, a recycling tray, a chimney tray, a jet tray, a turbogrid tray, a ripple tray, a dual flow tray, and a baffle tray, and usable packed towers include those packed with rings, saddles, Spraypak, Panapak, Goodloe packing, Stedmann packing, Dixon ring, MacMahon packing, Sulzer packing, helix (spiral rings), and vertical flat packing. Where a solid acid catalyst is used, it is desirable to use a layer packed with the catalyst and a rectification layer, i.e., a packed layer, a plate layer or a combination thereof.

The process of the present invention may be carried out either continuously or discontinuously. Continuous operation is preferred from the standpoint of productivity and running stability.

Where, for example, a nonvolatile liquid acid catalyst, such as sulfuric acid, is used, acetaldehyde, methanol and the liquid acid catalyst are fed either separately or as a mixture thereof to an arbitrary place of the tower, and the still is heated to an inner temperature of about 100° C. in the case of normal pressure. While the position for the starting materials and the catalyst to be introduced is not necessarily limited, methanol and acetaldehyde are preferably brought into countercurrent contact and to this effect the catalyst and methanol are preferably supplied from a position higher than the position where acetaldehyde is introduced.

When acetaldehyde contacts an acid in the absence of methanol, unfavorable side reactions such as coloration of the reaction mixture take place. It is therefore desirable that a liquid strong acid is diluted with methanol beforehand and then brought into contact with acetaldehyde.

Between the upper position where the catalyst and methanol are introduced and the top of the tower from which the acetal is distilled is provided a rectification portion with the number of theoretical plates necessary for separating water from the distillate, preferably 2 to 10 plates. Between the lower position where acetaldehyde is introduced and the bottom of the tower from which water is withdrawn is preferably provided a rectification portion having the number of theoretical plates necessary for separating methanol, etc. from water, preferably 2 to 10 plates.

Where a layer packed with a solid acid catalyst is separately provided to a part of the rectification tower, it is preferable to provide an inlet for methanol at the upper end of the catalyst layer and an inlet for acetaldehyde at the lower end.

While not limiting, the reflux ratio of the rectification tower portion preferably ranges from 0.2 to 8 and more preferably 0.5 to 4.

Thus, a mixture containing the acetal and methanol which has been charged in excess and containing substantially no acetaldehyde or water is obtained from the top of the rectification tower portion, while giving water from the bottom. In the case of using a homogeneous catalyst, such as sulfuric acid, an aqueous solution of the acid is discharged from the bottom.

Methanol is fed in excess over the stoichiometric amount in order to shift the equilibrium. The best results would be obtained by using 2 to 4 mols of methanol per mol of acetaldehyde. With the methanol to acetaldehyde molar ratio of less than 2, the unreacted acetaldehyde tends to distill from the top of the tower, resulting in a reduction in acetaldehyde conversion. If the molar ratio exceeds 4, the methanol content in the distillate tends to increase, resulting a reduction in productivity.

Presence of a small amount of the acetal or water in the starting materials, i.e., acetaldehyde and methanol, does not substantially interfere with carrying out the present invention. Note that presence of a large quantity of water in the starting materials results in an increased burden to the reactive distillation tower.

The starting materials may be fed either as liquids or after vaporized.

The reaction is carried out at the boiling point of the reaction system under the reaction pressure. For example, the reaction under normal pressure is desirably performed while controlling the reaction temperature within a range of from 50° to 70° C. The reaction time usually ranges from about 0.2 to 30 minutes in terms of a contact time, though varying depending on the amount of the catalyst used, the reaction temperature, and so on.

The reactive distillation is preferably conducted under normal pressure. Pressure application or pressure reduction is permitted, but reduced pressure decreases the inner temperature of the tower (i.e., the reaction temperature), which reduces the reaction rate and makes it necessary to decrease the temperature of a coolant of a reflux condenser. The reaction under pressure requires a more expensive apparatus.

According to the process of the present invention, the acetal is obtained from the top of the reactive distillation tower in the form of a mixture with methanol.

In carrying out azeotropic distillation of the acetal-methanol mixed system, the present inventors have found that n-hexane or cyclohexane out of a number of organic solvents is an azeotrope former which is capable of forming an azeotrope with methanol and a small amount of the acetal at an azeotropic point lower than that of a methanol/acetal azeotrope by a sufficient temperature difference and is inert to the acetal and that the n-hexane or cyclohexane used as an azeotrope former can effectively be recovered and reused in the acetal separation line.

More specifically, n-hexane forms an azeotrope with methanol and the acetal at 48° C. under normal pressure to provide an n-hexane/methanol/acetal composition of about 70/25/5 by weight; and cyclohexane forms an azeotrope with methanol and the acetal at 56° C. under normal pressure to provide a cyclohexane/methanol/acetal composition of about 53/30/17 by weight. An effective process has thus been established by taking advantage of these azeotropic characteristics.

Accordingly, in a preferred embodiment of the present invention, the distillate mainly comprising the acetal and methanol is subjected to azeotropic distillation in the presence of n-hexane or cyclohexane as an azeotrope former to separate the methanol as an azeotrope with n-hexane or cyclohexane and a small amount of the acetal from the top of a distillation tower and to recover the acetal as a bottom.

In a more preferred embodiment, the above separated azeotrope comprising methanol and n-hexane or cyclohexane as main components and a small amount of the acetal is then brought into countercurrent contact with water in an extraction tower, whereby methanol is separated from the lower part of the tower and a lighter liquid mainly comprising n-hexane or cyclohexane is recovered from the top of the tower, which is reused as an azeotrope former.

The above-described preferred and more preferred embodiments will be described below in detail.

Methanol, the acetal, n-hexane, and cyclohexane have a boiling point of 64.7° C., 64.3° C., 69° C., and 81° C., respectively, under normal pressure; and a methanol/acetal azeotrope (methanol content: 24 wt %) and an n-hexane/acetal azeotrope (n-hexane content: 30 wt %) have a boiling point (azeotropic point) of 57.5° C. and 64° C., respectively, under normal pressure, while an n-hexane/methanol azeotrope (methanol content: 28 wt %) and a cyclohexane/methanol azeotrope (methanol content: 38 wt %) have a boiling point (azeotropic point) of 50° C. and 54° C., respectively, under normal pressure. The present inventors have ascertained that n-hexane is capable of forming an azeotrope with methanol and a small amount of the acetal at a composition of about 70/25/5 by weight at an azeotropic point of about 48° C. and that cyclohexane is also capable of forming an azeotrope with methanol and a small amount of the acetal at a composition of about 53/30/17 by weight at an azeotropic point of about 56° C.

n-Hexane or cyclohexane is added to the acetal-methanol mixture in an amount sufficient for the whole amount of the methanol in the mixture to form an azeotropic mixture therewith. Addition of the azeotrope former in too large an excess increases the burden of the distillation system.

With the essential purpose of isolating the acetal as much as possible in mind, n-hexane is preferable to cyclohexane since the former forms an azeotrope having a smaller acetal content than the latter.

While not limiting, the distillation apparatus to be used in this embodiment is usually a rectification tower having about 1 to 100, preferably 5 to 50, theoretical plates. The rectification tower to be used is not strictly limited and may have any of the structures described above with reference to the reactive distillation tower.

The distillation may be under pressure or reduced pressure but is preferably conducted under normal pressure. The distillation may be carried out either continuously or discontinuously. Continuous operation is preferred from the standpoint of productivity and running stability. The reflux ratio is not particularly limited and is usually from about 1 to 10, though somewhat varying depending on the performance of the rectification tower.

The distillate which is an azeotrope comprising methanol and n-hexane or cyclohexane as main components and a small amount of the acetal (hereinafter referred to as an oil layer) is then brought into countercurrent contact with water in an extraction tower to separate and recover the n-hexane or cyclohexane as an oily phase. By this extraction with water, almost all of the methanol and the most of the acetal in the oil layer are withdrawn together with water from the bottom of the extraction tower as an aqueous phase while a lighter oily phase substantially comprising n-hexane or cyclohexane is recovered from the top of the tower, which can be reused as an azeotrope former.

Since the acetal is extremely labile against an acid, a small amount of a basic substance, such as sodium carbonate, sodium hydrogencarbonate, or sodium phosphate, may be added to extracting water so as not to lower the pH of the water below 7. It should be noted, however, that addition of a large amount of an inorganic salt inclusive of a neutral inorganic salt such as sodium chloride must be avoided because such produces a salting out effect to reduce the water solubility of methanol, etc.

While not limiting, the extracting temperature usually ranges from 10° to 50° C., and preferably from 15° to 45° C. At an extracting temperature lower than 10° C., the oil layer to be extracted tends to be separated into two layers. At an extracting temperature exceeding 50° C., the vapor pressure of the oil layer becomes high. The extraction may be carried out under reduced pressure or normal pressure or under pressure. Normal pressure is usually employed. The contact of water and the oil layer may be either in a batch system or in a continuous system. From the standpoint of productivity and running stability, a continuous system is desirable.

The extraction is preferably carried out in a countercurrent system by means of an extraction tower, in which the oil layer is fed from the lower part thereof and water is fed from the upper part thereof. The number of theoretical plates of the extraction tower is preferably about 2 to 10.

The structure of the extraction tower is not strictly restricted. Usable extraction towers include countercurrent differential type extraction towers, such as a spray tower, a packed tower, and a pulsed packed tower; non-stirring type plate towers, such as a perforated plate tower and a baffle tower; and a stirring type plate towers, such as a Scheiber tower, a rotating disc extraction tower, an Oldshue-Rushton tower, a Graesser extractor, an ARD tower, a Kühni tower, a pulsed perforated plate tower, a pulsating plate tower, and an alternating pulsating flow type extraction tower.

Feed rates of water and the oil layer to the extraction tower per unit time are decided according to the capacity and extraction ability of the tower, etc. A weight ratio of water to the oil layer to be fed is usually from 1:1 to 1:50, and preferably from 1:5 to 1:30. If the water feed is too low, methanol cannot be sufficiently extracted, resulting in an increased methanol content of the resulting oily phase. If it is too high, the load of recovery of methanol from the extracted aqueous phase increases.

The thus separated oily phase comprises n-hexane or cyclohexane with a trace amount of the acetal. Containing substantially no water or methanol, it can be used as such as an azeotrope former in the preceding distillation step. If an oily phase as containing a considerable amount of water is used as an azeotrope former in the preceding distillation step, the acetal obtained from the bottom of the distillation tower will have an increased water content and gradually undergoes hydrolysis, resulting in a reduction in yield. If the oily phase has a high methanol content, the amount of methanol circulating through the process line will increase only to increase the burden of the distillation tower of the preceding step, and the like.

The extracted aqueous phase, mainly comprising methanol, may be used as recovered as the starting material for acetal production. If desired, the aqueous phase may be once subjected to distillation to remove water and to increase the methanol concentration and then used as the starting material.

The present invention will be explained more specifically by referring to a typical embodiment for production and separation of a high purity acetal in which sulfuric acid is used as a catalyst and n-hexane is used as an azeotrope former. Reference is made to FIG. 1. In FIG. 1, A, B, and C indicate a reactive distillation tower, a distillation tower, and an extraction tower, respectively, and the solid lines and numerals 1 to 9 show flows of substances.

Step 1 (Acetal Formation)

Into reactive distillation tower A are continuously fed requisite amounts of acetaldehyde 2 and methanol. Methanol to be fed is a mixture of methanol 9 recovered from extraction tower C which contains a small amount of acetal and water and a necessary amount of fresh methanol 1. Methanol (1+9) has dissolved therein a requisite amount of sulfuric acid as a catalyst. The water content in methanol 9 and the produced water (inclusively indicated by numeral 3) is discharged from the bottom of the tower. If necessary, the thus discharged water containing the catalyst (sulfuric acid) is subjected to an appropriate treatment for disposal, such as neutralization, and then disposed.

Step 2 (Separation of High Purity Acetal)

Reaction mixture 4 comprising methanol and the acetal is introduced into distillation tower B together with liquid 8 which has been recovered from countercurrent extraction tower C as an oily phase and comprises n-hexane containing a trace amount of the acetal, where reaction mixture 4 is subjected to distillation under normal pressure. High purity acetal 5 is recovered from the bottom of the tower, and n-hexane is distilled from the top as three-component azeotrope 6 comprising n-hexane, methanol, and the acetal. The feed rate of the n-hexane-containing liquid 8 is adjusted to give a sufficient amount of n-hexane to form the three-component azeotrope.

Step 3 (Recovery of n-Hexane)

Three-component azeotrope 6 obtained from the top of distillation tower B is then brought into countercurrent contact with a small amount of water 7 in countercurrent extraction tower C. Almost all of the methanol and the most of the acetal are thus extracted into water to form an aqueous phase, which is withdrawn from the bottom of the tower as heavier liquid 9 and returned to reactive distillation tower A as a part of the methanol source. The oily phase substantially comprising n-hexane is recovered as lighter liquid 8 from the top of the tower and reused as an azeotrope former in Step 2.

Figure 2:
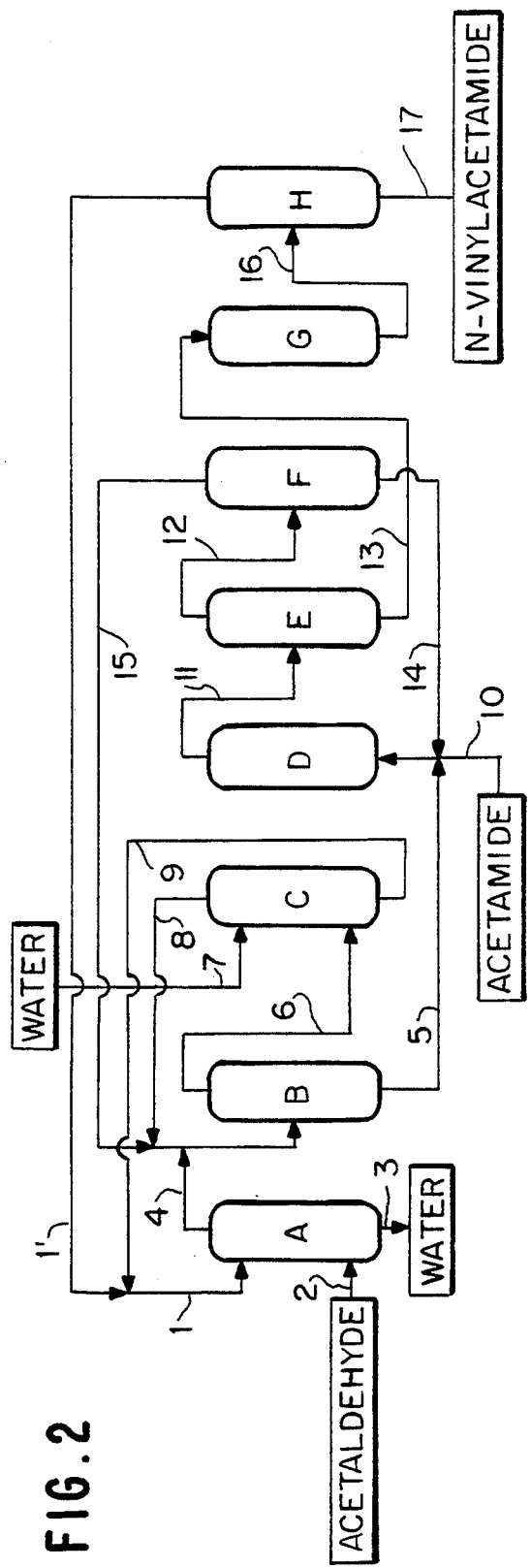
FIG. 2 is a flow diagram in which the acetal produced by the process of the present invention is used for the production of N-vinylacetamide, a starting material of hydrophilic polymers.

An application embodiment in which the acetal produced by the process of the present invention is used for the production of N-vinylacetamide, a starting material for hydrophilic polymers, will be illustrated below with reference to FIG. 2. In FIG. 2, A indicates a reactive distillation tower; B a distillation tower; C an extraction tower; D an ether-amidation reactor; E an acetal recovery tower; F a methanol recovery tower; G an ether-amide decomposition reactor; and H an N-vinylacetamide distillation tower. The solid lines and numerals 1 to 17 show flows of substances.

Step 1 (Acetal Formation)

A requisite amount of acetaldehyde 2 is continuously fed to reactive distillation tower A from the lower part thereof, and methanol 1, which is a mixture of methanol 9 recovered from extraction tower C and containing a small amount of the acetal and water and methanol 1' recovered from N-vinylacetamide distillation tower H, is simultaneously introduced into the tower from the upper part thereof. Methanol 1 (9+1') has dissolved therein a requisite amount of an acid catalyst, e.g., sulfuric acid. The water content which has previously been present in the methanol source and the produced water (inclusively indicated by numeral 3) is discharged from the bottom of the tower. If necessary, the thus discharged water containing the catalyst (sulfuric acid) is subjected to an appropriate treatment for disposal, such as neutralization, and then disposed.

Step 2 (Separation of High Purity Acetal)

Reaction mixture 4 comprising methanol and the acetal and methanol/acetal azeotrope 15 recovered from methanol recovery tower F are introduced into distillation tower B together with lighter liquid 8 from extraction tower C which comprises n-hexane containing a trace amount of the acetal. In distillation tower B, the methanol-acetal mixed system is subjected to distillation in the presence of n-hexane under normal pressure. High purity acetal 5 is recovered from the bottom of the tower, and methanol is distilled from the top as three-component azeotrope 6 comprising n-hexane, methanol, and a small amount of the acetal. The n-hexane feed is adjusted to give an amount necessary to form the three-component azeotrope.

Step 3 (Recovery of n-Hexane)

Three-component azeotrope 6 obtained from the top of distillation tower B is then brought into countercurrent contact with a small amount of water 7 in extraction tower C. Almost all of the methanol and the most of the acetal are thus extracted into water to form an aqueous phase, which is withdrawn from the bottom of the tower as heavier liquid 9 and returned to reactive distillation tower A as a part of the methanol source. The oily phase substantially comprising n-hexane is recovered as lighter liquid 8 from the top of the tower and reused as an azeotrope former in Step 2.

Step 4 (α-Methoxyethylacetamide (hereinafter abbreviated as MEA) Synthesis)

MEA is synthesized through an interchange reaction between the acetal and acetamide in accordance with a known process (e.g., U.S. Pat. No. 4,554,377).

The reaction is attended by by-production of methanol in an equimolar amount to MEA. Since acetamide and MEA have very close vapor pressures and also close solubilities in various solvents, it is difficult to separate them by distillation or recrystallization. Therefore, it is desirable to increase the acetamide conversion as high as possible, for example to 95% or higher. To this effect, the recommended amount of the acetal ranges from about 15 to 25 mols, and preferably from 18 to 22 mols, per mol of acetamide. If the acetal to acetamide molar ratio is less than 15, a sufficient acetamide conversion cannot be reached. If it exceeds 25, a significant improvement in acetamide conversion is no more obtained for the reduction in productivity.

Addition of a small amount of methanol to the reaction system is preferred. According to the common knowledge in the art, addition of methanol is not favorable because the interchange reaction between the acetal and acetamide is an equilibrium reaction. The preference of the methanol addition contrary to the common knowledge is based on the following reason. The produced MEA undergoes a further reaction with acetamide to by-produce ethylidenebisacetamide (hereinafter abbreviated as EBA) having extremely low solubility in the acetal. The reaction of EBA formation is also an equilibrium reaction. If there is no methanol in the reaction system, the by-produced EBA precipitates in the reaction system and no more participates in this equilibrium reaction. It follows that the equilibrium reaction is shifted to the production of EBA, resulting in a reduction of MEA yield. In order to dissolve the trace amount of the by-produced EBA so as to make it participate in the equilibrium reaction, it is desirable to add methanol in an amount of from about 1.2 to 5 mols per mol of acetamide. In general, the starting reaction system suitably contains 15 to 25 mols, preferably 18 to 22 mols of acetal and 1.2 to 5 mols, preferably 2 to 4 mols of metal, per mol of acetamide.

High purity acetal 5 obtained from the bottom of distillation tower B, acetal 14 obtained from the bottom of methanol recovery tower F which contains a small amount of methanol, and acetamide 10 are fed to ether-amidation reactor D packed with a strongly acidic ion exchange resin, e.g., Amberlist 15, to conduct MEA synthesis. From the outlet of ether-amidation reactor D is obtained reaction mixture 11 comprising MEA, the unreacted acetal, methanol produced by the reaction, and a trace amount of the unreacted acetamide.

Step 5 (Acetal Recovery)

Reaction mixture 11 from ether-amidation reactor D is introduced into distillation tower E for acetal recovery, where it is separated by simple distillation into acetal fraction 12 containing a small amount of methanol as a distillate and MEA 13 as a bottom.

Step 6 (Methanol Recovery)

Acetal fraction 12 containing a small amount of methanol which is obtained from the top of acetal recovery distillation tower E is fed to methanol recovery tower F to obtain methanol/acetal azeotrope 15 from the top of the tower, which is returned to Step 2 (separation of high purity acetal) where it is purified to a high purity acetal. Acetal 14 with a smaller methanol content which is obtained from the bottom of methanol recovery distillation tower F is forwarded to ether-amidation reactor D for reuse as a starting material of the ether-amidation reaction.

Step 7 (N-Vinylacetamide Synthesis)

MEA 13 from the bottom of acetal recovery distillation tower E is introduced into ether-amide decomposition reactor G, where MEA is thermally decomposed or catalytically decomposed in the presence of an acid catalyst into N-vinylacetamide and methanol. N-Vinylacetamide is recovered in the form of methanol solution 16 from the outlet of reactor G.

Step 8 (N-Vinylacetamide Purification)

N-Vinylacetamide methanol solution 16 obtained from reactor G is then subjected to distillation under reduced pressure in N-vinylacetamide distillation tower H and separated into methanol 1' (distillate) and N-vinylacetamide 17 (bottom). Methanol 1' recovered from the top of tower H is returned to reactive distillation tower A for Step 1 (acetal reaction)

The present invention is now illustrated in greater detail with reference to Examples, but it should be understood that the present invention is not construed as being limited thereto. All the percents are by weight unless otherwise indicated.

EXAMPLE 1

Methanol containing 0.5% sulfuric acid was fed to the 5th plate from the top of a 25-plate Oldershaw rectification tower at a feed rate of 180 g/hr, and acetaldehyde was fed to the 15th plate from the top at a feed rate of 72 g/hr. The bottom of the rectification tower was fitted with a 500 ml flask containing 100 g of water. The flask was heated to 100° C., and the content was withdrawn at a rate of 29 g/hr. In the stationary state, the liquid withdrawn from the flask contained substantially no organic substance. An acetal/methanol mixture was distilled from the top of the tower at a rate of 221 g/hr with a reflux ratio of 2. The distillate contained substantially no water or acetaldehyde. The acetaldehyde conversion was 100%, and the acetal yield was 100%.

EXAMPLE 2

The same operation as in Example 1 was conducted, except for feeding 112 g/hr of methanol containing 0.5% sulfuric acid to the 5th plate from the top and feeding 72 g/hr of acetaldehyde and 52 g/hr of methanol to the 15th plate from the top. The acetal was quantitatively obtained from the top of the tower.

EXAMPLE 3

A rectification tower having 30 theoretical plates and packed with 5 mm Raschig rings was used. Methanol containing 0.3% sulfuric acid was fed to the 10th theoretical plate at a feed rate of 112 g/hr, and acetaldehyde and methanol were fed to the 20th theoretical plate at a feed rate of 72 g/hr and 52 g/hr, respectively. The acetal was quantitatively obtained from the top of the tower.

EXAMPLE 4

A reactor composed of a 10-plate Oldershaw rectification tower, a 10-theoretical plate tower packed with Amberlist 15 (produced by Rohm & Haas), and a 10-plate Oldershaw rectification tower in sequence was used. Acetaldehyde and methanol were fed to the 10th plate and 20th plate from the bottom of the reactor, respectively, at a feed rate of 71.7 g/hr and 180 g/hr, respectively, and reacted continuously at a reflux ratio of 2. As a result, the acetal was quantitatively obtained from the top of the tower at an acetaldehyde conversion of 100%.

EXAMPLE 5

The same operation of Example 4 was conducted, except for replacing Amberlist 15 with Nafion H (produced by Dow Chemical Co.) as a catalyst. As a result, the acetal was quantitatively obtained from the top of the tower at an acetaldehyde conversion of 100%.

EXAMPLE 6

The same operation as in Example 4 was conducted, except for using a packed rectification tower having 10 theoretical plates and packed with 5 mm Raschig rings in place of the Oldershaw rectification tower. The acetal was quantitatively obtained from the top of the tower at an acetaldehyde conversion of 100%.

EXAMPLE 7

The same operation as in Example 4 was conducted, except for using a packed rectification tower having 25 theoretical plates and packed with crystalline aluminosilicate cylinders having a diameter of 5 mm in place of the Oldershaw rectification tower. The acetal was quantitatively obtained from the top of the tower at an acetaldehyde conversion of 100%.

Reference Example

In a three-necked flask were charged 128 g of methanol and 0.86 g of sulfuric acid and heated to 55° C. To the solution was added dropwise 44 g of acetaldehyde over 30 minutes. After the addition, the reaction was further continued for an additional period of 1 hour. At this point, the acetaldehyde conversion and the acetal selectivity were found to be 78% and 98%, respectively, and the content of condensation by-products was 1% (based on the weight of acetaldehyde). The reaction mixture was further allowed to react for an additional period of 3 hours. At this point, the acetaldehyde conversion and the acetal selectivity were 75% and 95%, respectively, and the content of condensation by-products increased to 3% (based on the weight of acetaldehyde). These results practically agreed with those obtained from the equilibrium constant among acetaldehyde, methanol, water, and the acetal, indicating that the reaction had reached the equilibrium state.

EXAMPLE 8

A 25-plate glass-made Oldershaw rectification tower (column diameter: 30 mm) was used. n-Hexane was fed to the first plate from the top at a feed rate of 56 g/hr, and methanol and the acetal were fed to the 10th plate from the top at a feed rate of 20 g/hr and 51 g/hr, respectively. The tower was heated so as to maintain a reflux ratio of 6 and the tower top temperature of 50° C. The bottom of the tower was fitted with a 500 ml flask containing 100 g of the acetal, and the flask was heated in an oil bath at 110° C. The content of the flask was withdrawn at a rate of 47 g/hr. The liquid withdrawn from the flask comprised the acetal containing substantially no n-hexane and containing 0.3% methanol. An acetal/methanol/n-hexane mixture was obtained from the top of the tower at a rate of 80 g/hr.

When the position of n-hexane introduction was changed to the 10th plate from the top, the similar results were obtained.

EXAMPLE 9

Cyclohexane was fed to the first plate from the top of the same rectification tower as used in Example 8 at a rate of 35 g/hr, while feeding methanol and the acetal to the 10th plate from the top at a rate of 20 g/hr and 51 g/hr, respectively. Heating was conducted so as to maintain the tower top temperature at 57° C. at a reflux ratio of 6. A 500 ml flask containing 100 g of acetal was provided at the bottom of the tower and heated in an oil bath at 110° C., and the content of the flask was withdrawn at a rate of 40 g/hr. The liquid withdrawn from the flask was the acetal containing 0.5% methanol with no substantial cyclohexane content. An acetal/methanol/cyclohexane mixture was obtained from the top at a rate of 66 g/hr.

When the position of cyclohexane introduction was changed to the 10th plate from the top, the similar results were obtained.

EXAMPLE 10

Step 1

Methanol containing 0.5% sulfuric acid was fed to the 5th plate from the top of a 25-plate Oldershaw rectification tower at a rate of 180 g/hr, while feeding acetaldehyde to the 15th plate from the top at a rate of 72 g/hr. A 500 ml flask containing 100 g of water was provided at the bottom of the tower and heated to 100° C., and the content of the flask was withdrawn at a rate of 29 g/hr. The liquid withdrawn from the flask contained no substantial organic substance. An acetal/methanol mixture was obtained from the top at a rate of 221 g/hr at a reflux ratio of 2. The distillate contained substantially no water or acetaldehyde. The acetaldehyde conversion and the acetal yield were 100% and 100%, respectively.

Step 2 n-Hexane was fed to the first plate from the top of a 25-plate glass-made Oldershaw rectification tower at a rate of 56 g/hr, while feeding the acetal/methanol mixture obtained in Step 1 above (methanol content: 28%) to the 10th plate from the top at a rate of 71 g/hr. Heating was conducted so as to maintain the tower top temperature at 50° C. at a reflux ratio of 6. A 500 ml flask containing 100 g of the acetal was provided at the bottom of the tower and heated in an oil bath at 110° C., and the content of the flask was withdrawn at a rate of 47 g/hr. The liquid withdrawn from the flask was the acetal containing 0.3% methanol with no substantial n-hexane content. An acetal/methanol/n-hexane mixture was obtained from the top of the tower at a rate of 80 g/hr. Both the distillate and the bottom contained substantially no water or acetaldehyde.

Step 3

A liquid-liquid countercurrent extractor having a tower inner diameter of 50 mm and fitted with 30 baffle plates at 25 mm intervals was used. The distillate obtained in Step 2 was fed as a lighter liquid from the lower part of the extraction tower at a rate of 2370 g/hr, and water as a heavier liquid was fed from the upper part of the tower at a rate of 153 g/hr to conduct countercurrent extraction. The baffle plates were given up-and-down movement at a 12.5 mm stroke to make 150 cycles. The lighter liquid after extraction was n-hexane containing substantially no water or methanol and containing 3% of the acetal. The extracted heavier liquid comprised 80% of methanol, 5% of the acetal, 1% of n-hexane and water as the remainder.

EXAMPLE 11

Step 1

Methanol containing 0.5% sulfuric acid was fed to the 5th plate from the top of a 25-plate glass-made Oldershaw rectification tower at a rate of 180 g/hr, while feeding acetaldehyde to the 15th plate from the top at a rate of 72 g/hr. A 500 ml flask containing 100 g of water was provided at the bottom of the tower and heated to 100° C., and the content of the flask was withdrawn at a rate of 29 g/hr. The liquid withdrawn from the flask contained no substantial organic substance. An acetal/methanol mixture was obtained from the top at a rate of 221 g/hr at a reflux ratio of 2. The distillate contained substantially no water or acetaldehyde. The acetaldehyde conversion and the acetal yield were 100% and 100%, respectively.

Step 2 n-Hexane was fed to the first plate from the top of a 25-plate glass-made Oldershaw rectification tower at a rate of 56 g/hr, while feeding the acetal/methanol mixture obtained in Step 1 above (methanol content: 28%) to the 10th plate from the top at a rate of 71 g/hr. Heating was conducted so as to maintain the tower top temperature at 50° C. at a reflux ratio of 6. A 500 ml flask containing 100 g of the acetal was provided at the bottom of the tower and heated in an oil bath at 110° C., and the content of the flask was withdrawn at a rate of 47 g/hr. The liquid withdrawn from the flask was the acetal containing 0.3% methanol with no substantial n-hexane content. An acetal/methanol/n-hexane mixture was obtained from the top of the tower at a rate of 80 g/hr. Both the distillate and the bottom contained substantially no water or acetaldehyde.

Step 3

A liquid-liquid countercurrent extractor having a tower inner diameter of 50 mm and fitted with 30 baffle plates at 25 mm intervals was used. The distillate obtained in Step 2 was fed as a lighter liquid from the lower part of the extraction tower at a rate of 2370 g/hr, and water as a heavier liquid was fed from the upper part of the tower at a rate of 153 g/hr to conduct countercurrent extraction. The baffle plates were given up-and-down movement at a 12.5 mm stroke to make 150 cycles. The lighter liquid after extraction was n-hexane containing substantially no water or methanol and containing 3% of the acetal. The extracted heavier liquid comprised 80% of methanol, 5% of the acetal, 1% of n-hexane and water as the remainder.

Step 4 (MEA Synthesis)

The high purity acetal obtained in Step 2 was mixed with the methanol-containing acetal obtained in the methanol recovery step hereinafter described, and dried acetamide was dissolved therein to prepare a starting mixture having an acetamide/acetal/methanol molar ratio of 1/20/3. The mixture was fed to the lower part of a jacketed reaction tower having an inner diameter of 40 mm and packed with 60 ml of a strongly acidic ion exchange resin "Amberlist 15" at a rate of 5 ml/hr. Warm water at 55° C. was circulated in the jacket of the reactor to keep the reaction temperature at that temperature. Quantitative determination of the reaction mixture obtained from the upper part of the reactor revealed an acetal/methanol/MEA molar ratio of about 19/4/0.9, indicating 98% of the acetamide conversion and 90% of the MEA yield.

Step 5 (Acetal Recovery)

The reaction mixture obtained in Step 4 was supplied at a rate of 600 g/hr to a jacketed continuous flash evaporator of thin film type having a heat conduction area of 0.04 m² having been evacuated to 100 mmHg. A heating medium at 90° C. was circulated through the jacket. An evaporation residue substantially comprising MEA was obtained at a rate of 17 g/hr. A condensate of the volatile components which comprised 7% methanol-containing acetal was obtained at a rate of 583 g/hr.

Step 6 (Methanol Recovery)

The 7% methanol-containing acetal fraction obtained from Step 5 was introduced into the 10th plate from the top of a 25-plate glass-made Oldershaw rectification tower at a rate of 200 g/hr. Heating was conducted at a reflux ratio of 6 to maintain the tower top temperature at 58° C. A 500 ml flask was provided at the bottom of the rectification tower and heated in an oil bath at 110° C. The content of the flask was withdrawn at a rate of 185 g/hr. The liquid withdrawn from the flask was the acetal containing 5.6% methanol. An acetal/methanol azeotrope containing 24% methanol was obtained from the top of the tower at a rate of 15 g/hr.

Step 7 (N-Vinylacetamide Synthesis)

The liquid substantially comprising MEA obtained in Step 5 was supplied to a stainless steel reactor having an inner diameter of 25 mm and a total length of 2 m which had been heated to 450° C. and evaluated to 400 mmHg at a rate of 20 ml/hr. The mixture of N-vinylacetamide and methanol resulting from the thermal decomposition reaction was condensed in a cooler provided at the outlet of the reactor and thus recovered. The MEA conversion was 95%. Step 8 (Purification of N-Vinylacetamide)

The reaction mixture obtained in Step 7 was introduced into the 10th plate from the top of a 10-plate glass-made Oldershaw rectification tower at a rate of 200 g/hr. The tower was kept under reduced pressure of 200 mmHg, and the top temperature was maintained at 40° C. at a reflux ratio of 2. A 500 ml flask was provided at the bottom of the tower and heated in an oil bath at 80° C. The content of the flask was withdrawn at a rate of 155 g/hr. The liquid withdrawn from the flask was a methanol solution containing 94% of N-vinylacetamide. Methanol was distilled from the top of the tower at a rate of 45 g/hr.

The liquid from the flask (94% N-vinylacetamide-containing methanol solution) was further introduced at a rate of 155 g/hr into the 10th plate of a rectification tower having 20 theoretical plates and packed with 5-mm Sulzer packing. The tower was kept under reduced pressure of 2 mmHg and at a reflux ratio of 3. A 500 ml flask was provided at the bottom of the rectification tower and heated in an oil bath at 105° C. The content of the flask was withdrawn at a rate of 140 g/hr. The liquid withdrawn from the flask was N-vinylacetamide. Methanol containing a small amount of acetamide was distilled from the top of the tower at a rate of 15 g/hr.

EXAMPLE 12

N-vinylacetaldehyde was obtained in the same manner as in Example 11, except for using cyclohexane in place of n-hexane in Steps 2 and 3.

The advantages of the present invention owe much to the use of methanol as a starting material. Besides being the most easily available and cheap alcohol, methanol makes a great contribution to efficient separation of the product after the reaction. The advantages of the present invention also owe to adoption of a reactive distillation system for lifting the limit of a conversion associated with an equilibrium reaction. In the embodiment in which the acetal product is isolated by using n-hexane or cyclohexane as an azeotrope former, the unreacted methanol and the product whose boiling points are very close to each other can be separated with good efficiency, and n-hexane or cyclohexane in the resulting azeotropic mixture can effectively be recovered by countercurrent contact with water. The thus separated and recovered components can be reused as an azeotrope former and a starting material. Thus, the present invention provides the most suitable combination of a starting material, a reaction operation, separation and recovery steps, and the like to establish an industrially advantageous production line as a whole, making it possible to obtain dimethylacetal useful as, e.g., an intermediate for N-vinylacetamide with ease and simpleness and in satisfactory final yield on an industrial scale.

While the invention has been described in detail and with reference to specific examples thereof, it will be apparent to one skilled in the art that various changes and modifications can be made therein without departing from the spirit and scope thereof.

What is claimed is:

1. A process for producing acetaldehyde dimethylacetal comprising reacting acetaldehyde and methanol in the presence of an acid catalyst in a part of a rectification tower while conducting rectification to withdraw the water by-produced from the bottom of the tower and to recover a distillate containing the acetaldehyde dimethylacetal produced from the top of the tower, wherein said acid catalyst is a solid acid catalyst packed in a part of the rectification tower, and said acetaldehyde and methanol are continuously fed to said solid acid catalyst layer.

2. A process as claimed in claim 1, wherein said acid catalyst is a nonvolatile liquid acid catalyst, and said acetaldehyde, methanol and acid catalyst are continuously fed to a part of the rectification tower.

3. A process as claimed in claim 1 which further includes a step in which the distillate mainly comprising the acetaldehyde dimethylacetal and methanol is subjected to azeotropic distillation in the presence of n-hexane or cyclohexane as an azeotrope former to separate the methanol as an azeotrope with n-hexane or cyclohexane and a small amount of the acetaldehyde dimethylacetal as a distillate and to recover the acetaldehyde dimethylacetal as a bottom.

4. A process as claimed in claim 3 which further includes a step in which the azeotrope comprising methanol, n-hexane or cyclohexane, and a small amount of the acetaldehyde dimethylacetal is brought into contact with water to separate into an aqueous phase containing the methanol and an oily phase mainly comprising n-hexane or cyclohexane, said oily phase being reused as an azeotrope former.

5. A process for producing acetaldehyde dimethylacetal from acetaldehyde and methanol comprising steps of:
   1) continuously feeding acetaldehyde and methanol to a reactor to which a rectification tower is connected in series to conduct a reaction in the presence of an acid catalyst simultaneously with rectification to withdraw the water by-produced from the bottom of the tower and to recover a distillate containing the acetaldehyde dimethylacetal produced from the top of the tower,
   2) subjecting the distillate recovered in step (1) to azeotropic distillation in the presence of n-hexane or cyclohexane as an azeotrope former to distill an azeotrope comprising methanol, n-hexane or cyclohexane, and acetaldehyde dimethylacetal from the top of a distillation tower and to recover high purity acetaldehyde dimethylacetal as a bottom,
   3) bringing the distillate obtained in step (2) into contact with water to extract methanol into the aqueous phase and to recover n-hexane or cyclohexane as a lighter liquid, and
   4) recycling the n-hexane or cyclohexane recovered in step (3) to step (2) as an azeotrope former and recycling the methanol-rich aqueous phase to step (1).

6. A process for separating acetaldehyde dimethylacetal from a mixture mainly comprising acetaldehyde dimethylacetal and methanol, which comprises subjecting the mixture to azeotropic distillation in the presence of n-hexane or cyclohexane as an azeotrope former to obtain an azeotrope composed of methanol, n-hexane or cyclohexane, and a small amount of the acetaldehyde dimethylacetal as a distillate and high purity acetaldehyde dimethylacetal as a bottom.

7. A process as claimed in claim 6, which further includes a step in which the distillate comprising methanol, n-hexane or cyclohexane, and a small amount of the acetaldehyde dimethylacetal is brought into contact with water to separate into an aqueous phase containing the methanol and an oily phase mainly comprising n-hexane or cyclohexane, said oily phase being reused as an azeotrope former.

* * * * *